United States Patent [19]

Kerby

[11] 4,324,621

[45] Apr. 13, 1982

[54] METHOD AND APPARATUS FOR CONTROLLING THE QUALITY OF ELECTROLYTES

[75] Inventor: Robert C. Kerby, Rossland, Canada

[73] Assignee: Cominco Ltd., Canada

[21] Appl. No.: 163,282

[22] Filed: Jun. 26, 1980

Related U.S. Application Data

[63] Continuation-in-part of Ser. No. 107,180, Dec. 26, 1979, abandoned.

[51] Int. Cl.$^3$ .............................................. G01N 27/46
[52] U.S. Cl. ............................... 204/1 T; 204/DIG. 2
[58] Field of Search ........................... 204/1 T, DIG. 2

[56] References Cited

U.S. PATENT DOCUMENTS

| | | | |
|---|---|---|---|
| 1,465,034 | 8/1923 | Antisell | 204/DIG. 2 |
| 1,619,835 | 3/1927 | Summers | 204/DIG. 2 |
| 4,146,437 | 3/1979 | O'Keefe | 204/1 T |
| 4,217,189 | 8/1980 | Kerby | 204/119 |

*Primary Examiner*—R. L. Andrews

*Attorney, Agent, or Firm*—Wenderoth, Lind & Ponack

[57] ABSTRACT

A method and apparatus for controlling a process for the electrodeposition of metals using electrolyte containing concentrations of impurities and addition agents that affect polarization. The method and apparatus include a test circuit comprising a test cell, a sample of electrolyte, a moving cathode, an anode and a reference electrode immersed in said sample, a constant current source and measuring means electrically connected to the electrodes. A controlled low current is applied to the electrodes in the test cell to measure the activation overpotential between the cathode and the reference electrode. The activation overpotential is measured at the point of inchoate deposition of the metal and is related to the concentration of impurities and polarization affecting agents in the sample. The processes for the purification of electrolyte and the electrodeposition of metals are subsequently adjusted in relation to the measured value of the activation overpotential to obtain optimum metal deposition.

38 Claims, No Drawings

METHOD AND APPARATUS FOR CONTROLLING THE QUALITY OF ELECTROLYTES

CROSS-REFERENCE TO RELATED APPLICATIONS

This application is a Continuation-in-Part of my application Ser. No. 107,180 filed Dec. 26, 1979, and now abandoned.

BACKGROUND OF THE INVENTION (a) Field of the Invention

This invention relates to a method and apparatus for continuously monitoring the electrodeposition of metals and, more particularly, to a method for measuring the activation overpotential of metal deposition and controlling the electrolyte purification and electrodeposition processes in response to deviations of recorded values of the overpotential from the desired values, and an apparatus to carry out the method.

(b) Description of the Prior Art

In processes for electrodeposition of metals such as electrowinning, electro-refining and electro-plating, electrolytes are used which contain impurities which, when present above certain critical concentrations, can electrodeposit with the metal and thereby contaminate or cause re-solution of the deposit with a corresponding decrease in the efficiency of the metal deposition process. To reduce the concentration of impurities in the electrolyte purification procedures may be employed prior to electrolysis. In addition to the purification, one or more polarizing additives may be added to the electrolyte to assist in providing smooth and level deposits, as well as to reduce the effects of remaining impurities.

These polarizing additives act to change polarization. Polarization can be changed by increasing, or decreasing, the concentration of a polarization-causing agent. Polarization also can be changed by decreasing or increasing the concentration of a de-polarization-causing agent. These agents, both polarizing and de-polarizing, can be present in the electrolyte as it comes to the cells from the purification plant, or may be substances, such as animal glue, that are added to the electrolyte to effect control of the electrodeposition process. It is thus to be clearly understood that the term "polarization affecting agents" includes agents of both the polarization-causing and depolarization-causing types. It is also pertinent to note that a given substance will not always act in the same manner in different processes. Thus a substance may act as a polarization agent in one process, as depolarization agent in another process involving a different metal, or may be inactive in a third process. Similarly it is not unknown for impurities to "catalyse" the effects of polarization affecting agents. Thus it is well known that some experimentation may be needed in order to decide which polarization affecting agents are suitable for any given process.

The procedures presently used for determining the purity of electrolyte are based on chemical analyses and determination of current efficiencies as a measure of impurity content, while those for the addition of suitable polarization affecting agents are based simply on maintaining a constant concentration of agents in the electrolyte despite variations in the quality of the electrolyte. These procedures result in variations in the quality of the deposited metal and the efficiency of the electrodeposition process.

The prior art contains a number of references related to methods for determining the effects of impurities, and addition agents on electrodeposition processes for metals and for determining the purity of electrolyte solutions.

According to U.S. Pat. No. 3,925,168, L. P. Costas, Dec. 9, 1975, there is disclosed a method and apparatus for determining the content of colloidal material, glue or active roughening agent in a copper plating bath by determining the overpotential-current density relationships of solutions having varying known reagent content and comparing the results with that of a solution with a known plating behaviour and roughening agent content. According to Canadian Pat. No. 998,879, C. J. Krauss et al, May 11, 1976, there is disclosed a method for determining and controlling the cathode polarization voltage in relation to current density of a lead refinery electrolyte, wherein the slope of the polarization voltage-current density curve is a measure of the amount of addition agents and wherein the effectiveness of addition agents is changed when the cathode polarization voltage attains values outside the predetermined range of values.

A number of studies are reported in the published literature which relate to similar methods. C. L. Mantell et al (Trans. Met. Soc. of AIME, 236, 718-725, May 1966) determined the feasibility of current-potential curves as an analytical tool for monitoring manganese electrowinning solutions for metallic impurities. Polarization curves related to hydrogen evolution where shown to be sensitive to metallic impurities which affect the cathode surface thereby altering the hydrogen overvoltage. H. S. Jennings et al (Metallurgical Transactions, 4, 921-926, April 1973) describe a method for measuring cathodic polarization curves of copper sulfate solutions containing varying amounts of addition agents by varying an applied voltage and recording the relationship between voltage and current density. O. Vennesland et al (Acta Chem. Scand., 27, 3, 846-850, 1973) studied the effects of antimony, cobalt, and beta-naphthol concentrations in zinc sulfate electrolyte on the current-potential curve by changing the cathode potential at a programmed rate, recording the curves and comparing the curves with a standard. T. N. Anderson et al (Metallurgical Transactions B, 7B, 333-338, September 1976) discuss a method for measuring the concentration of glue in copper refinery electrolyte by determining polarization scan curves, which upon comparison provide a measure of glue concentration. According to U.S. Pat. No. 4,146,437 issued Mar. 27, 1979, T. J. O'Keefe, there is disclosed the use of cyclic voltammetry for the evaluation of zinc and copper sulfate electrolytes. Cyclic voltammograms, which include the cathodic of zinc and copper sulfate current-potential relationships, and polarization curves, are recorded as a means for approximating the quantities of impurities and addition agents in zinc sulfate electrolytes.

This first group of references discloses methods wherein metal is deposited on an electrode and wherein current, or current density-potential, curves represent cathode polarization potentials in relation to varying currents and/or current densities.

T. R. Ingraham et al (Can. Met. Quarterly, 11, 2, 451-454, 1972) describe a meter for measuring the quality of zinc electrolytes for measuring the amount of cathodic hydrogen released during electrodeposition of zinc and indicating current efficiency by comparing the weight of deposited zinc with both the amount of zinc to be expected and the rate of hydrogen evolution. In U.S. Pat. No. 4,013,412, Satoshi Mukae, Mar. 22, 1977, there is disclosed a method for judging purity of purified zinc sulfate solution by subjecting a sample of solution to electrolysis, combusting generated gases and measuring the internal pressure in the combustion chamber which is an indirect measure of current efficiency. M. Maja et al (J. Electrochem. Soc., 118, 9, 1538–1540, 1971) and P. Benvenuti et al (La Metallurgia Italiana, 60, 5, 417–423, 1968) describe methods for detection of impurities and measuring the purity of zinc sulfate solutions by depositing zinc and then dissolving deposited zinc electrolytically and relating calculated current efficiency to impurity content.

This second group of references relates to methods and apparatus for determining electrolyte purity wherein electrolysis of solutions is used to determine current efficiency which is subsequently related to electrolyte purity.

In my co-pending United States Application Ser. No. 052,921, filed June 26th, 1979, there is disclosed a method for controlling a process for the recovery of zinc from a zinc sulfate electrowinning solution which comprises decreasing a potential, which is applied between electrodes in a test cell containing a sample of solution, at a constant rate at substantially zero current, measuring the decreasing potential, terminating the decreasing of the potential at a value corresponding to the point at which zinc starts to deposit, determining the activation overpotential, relating the activation overpotential to the concentration of impurities and adjusting the process to obtain optimum recovery of zinc.

Although the method according to this co-pending application overcomes the necessity for electrolyzing solution to determine current efficiencies or for measuring polarization potentials in relation to varying currents or current densities, several disadvantages still exist. The method is not continuous and it is necessary to determine the value of the activation overpotential for each sample by decreasing the applied potential each time until the value is reached at which zinc starts to deposit and the current density increases from its substantially zero value for a further small decrease in potential.

SUMMARY OF THE INVENTION

I have now found that it is unnecessary to decrease the applied potential in order to determine the value of the activation overpotential. Thus, I have found that the activation overpotential can be measured as a function of time at a controlled, low current, and that the purification and electrodeposition processes can be controlled by correcting the amounts of reagents in response to deviations of recorded values of the overpotential from desired values in order to return to the desired optimum values.

The method and apparatus of the present invention apply to electrodeposition processes of metals employing electrolytes which are prepared for electroplating of metals; which are used in processes for the recovery of metals by electrowinning; or which are used in processes for the electro-refining of metals. In many cases, the electrodeposition processes include a purification process. The method and apparatus of the invention may be used in the electrodeposition processes for metals such as zinc, copper, lead, iron, cobalt, nickel, manganese, chromium, tin, cadmium, bismuth, indium, silver, gold, rhodium and platinum.

When metal-ion containing solution, or electrolyte, is subjected to a controlled low current applied to electrodes placed in a test cell containing electrolyte, and the current has a value which is sufficient to cause inchoate deposition of metal on a suitable cathode made of a material other than the metal being deposited, the value of the resulting potential represents the activation overpotential for the metal deposition onto the suitable cathode. When the cathode is a moving cathode, values of the activation overpotential can be measured and recorded and the electrodeposition process of the metal can be controlled in response to the measured and recorded values of the activation overpotential. Inchoate deposition is defined, for the purpose of this invention, as the deposition of metal which has just begun and is limited to partial covering of the moving cathode surface by metal. The measured values of the activation overpotential can be used as a direct measure of the impurity concentration, (i.e. the effectiveness of a purification process), of the polarization affecting agent concentration, and of the polarization affecting agent concentration relative to the impurity concentration in the electrolyte in a process for the electrodeposition of metal which includes a purification process. In response to measured values of the activation overpotential, several changes are possible, either alone, or in combination: the purification process can be adjusted; the concentration of polarization affecting agent in the electrolyte can be adjusted, or the concentration of polarization affecting agent in the electrolyte can be adjusted relative to the impurity concentration; and the impurity concentration can be adjusted, so that optimum efficiency and level metal deposits are obtained in the electrodeposition process.

DESCRIPTION OF THE PREFERRED EMBODIMENTS

Accordingly, there is provided a method for controlling a process for the electrodeposition of a metal using electrolyte containing concentrations of impurities, said method comprising the steps of establishing a test circuit comprising a test cell, a sample of electrolyte, a moving cathode, having an area exposed to said electrolyte, an anode and a reference electrode, said electrodes being immersed in said sample, a constant current supply and measuring means electrically connected to said electrodes; applying a low current to the electrodes in said test cell, said current being sufficient to cause inchoate deposition of said metal on said cathode; measuring the activation overpotential at the point of inchoate deposition of said metal; relating said activation overpotential to the concentration of impurities in said sample; and adjusting the process for the recovery of metal to obtain optimum deposition of metal, wherein inchoate deposition is defined as the deposition of metal which has just begun and is limited to a partial covering of the moving cathode surface by metal.

In a second embodiment, the method includes controlling a process for the electrodeposition of a metal using electrolyte containing concentrations of at least one polarization affecting agent; measuring the activation overpotential according to the said method; relating the measured activation overpotential to the concentration of said at least one polarization affecting agent in said sample; and adjusting the concentration of said polarization affecting agent in the electrolyte to obtain optimum efficiency and level metal deposits in the electrodeposition process, wherein inchoate deposition is defined as the deposition of metal which has just begun and is limited to a partial covering of the moving cathode surface by metal.

In a third embodiment, the method includes controlling a process for the electrodeposition of a metal using electrolyte containing concentrations of impurities and at least one polarization affecting agent; measuring the activation overpotential according to the said method; relating the measured activation overpotential to the concentration ratio between impurities and said at least one polarization affecting agent in said sample; and adjusting the concentration ratio in the electrolyte to obtain optimum efficiency and level metal deposits in the electrodeposition process, wherein inchoate deposition is defined as the deposition of metal which has just begun and is limited to a partial covering of the moving cathode surface by metal.

The invention will now be described in detail. The apparatus used in the method for measuring the activation overpotential of a metal consists of a test circuit which comprises a test cell, a sample of electrolyte, a moving cathode, an anode, a reference electrode, means to supply a constant current and means for measuring the activation overpotential. The test cell is a small container of circular, square or rectangular cross-section made of a suitable material, which is preferably resistant to corrosion by electrolyte and large enough to hold a suitable sample of electrolyte. If desired, the cell may be ventilated to remove evolved gas. Means are provided in the cell to make it possible to continuously add electrolyte to, and to discharge electrolyte from, the test cell. The three electrodes are immersed in the electrolyte sample and are removably positioned in the cell at constant distances from each other.

The moving cathode is made of an electrically conductive material other than the metal being deposited, which material is suitable for using in the electrodeposition process of the metal being deposited and which is compatible with the electrolyte used in the process. The material of the moving cathode may be made of the same material as is used for the cathode(s) in the electrodeposition process, provided that the material is different from the metal being deposited. For example, in the controlling of electrodeposition processes using sulfate-based electrolyte such as in processes for deposition of zinc, copper, manganese, nickel, cobalt, iron and cadmium, the moving cathode is preferably made of aluminum or a suitable aluminun alloy. If desired, a moving cathode of other suitable materials such as e.g. titanium, iron, steel, stainless steel, nickel, lead, copper and the like may be used in an electrodeposition process. A moving flexible plastic electrode of a suitable electroconductive material could also be used.

The moving cathode has a constant area of its surface in contact with electrolyte in the cell. I have determined that a surface area in contact with the cell electrolyte in the range of about 0.1 to 1 $cm^2$ gives excellent results. The moving cathode is preferably a wire or strip which is contained in and moves through a cathode holder. The holder envelopes the moving cathode except for the constant surface area which is in contact with electrolyte. Means are provided to move the moving cathode intermittently or continuously through the cathode holder and, consequently in contact with electrolyte. Preferably, these means include provisions to move the cathode continuously at a constant rate. The use of a moving cathode made of wire or strip has a number of advantages. No special preparation of the cathode surface is usually necessary, wire or strip is readily available at low cost and test results are reproducible. The moving cathode does not have to be replaced and thus allows intermittent or continuous operation. Most commercially available suitable cathode materials in the form of wire and strip are useful as long as they have sufficiently smooth and clean surfaces, possess good corrosion resistant properties in the electrolyte, are sufficiently ductile to be moved through the cathode holder and have electrochemical characteristics that produce reproducible test results.

The anode is made of a suitably inert material that allows gas evolution. For example, in sulfate electrolyte a suitable anode material may be a lead-silver alloy. I have found that, for sulfate electrolytes, anodes made of lead-silver alloy containing 0.75% silver are satisfactory and that for chloride-containing electrolytes, other than those containing concentrated hydrochloric acid, platinum is satisfactory. Other suitably inert materials for the anode include carbon and graphite. The reference electrode can be any one of a number of suitable reference electrodes such as, for example, a standard calomel electrode (SCE).

The three electrodes are electrically connected to a source of constant current and to measuring means for the activation overpotential. The source of constant current is connected to the anode and the moving cathode. The measuring means for the activation overpotential measures the overpotential on the moving cathode relative to the reference electrode. The measured activation overpotential may, for example, be recorded on a meter or other suitable read-out instrument, or alternatively may be recorded in the form of a line or trace as a function of time. The electrodes are removably positioned in the cell in fixed relation to each other. I have found that good results are obtained when the surface area of the moving cathode that is in contact with electrolyte is kept at a fixed distance of about 4 cm from the surface of the anode and when the reference electrode is positioned between the cathode and the anode in such a way that the tip of the reference electrode is rigidly located at a distance of about 1 cm from but not covering the surface area of the moving cathode in contact with electrolyte. If desired, a diaphragm or semi-permeable membrane may be positioned in the test cell between the anode and the cathode to provide separate anodic and cathodic compartments; the reference electrode is then placed in the cathodic compartment.

Suitable means may be provided to maintain the electrolyte in the cell at a suitable constant temperature. Such means may comprise controlled heating/cooling means for electrolyte prior to electrolyte entering the cell or a controlled heating/cooling coil placed in the test cell, or a constant temperature bath or the like.

In the method of the invention, a sample of electrolyte, which may be basic, neutral or acidic and which may contain addition agents, and which may be obtained from either an electrolyte purification process or a metal electrodeposition process, is added to the test cell. To ensure reproducible results, the sample is kept in motion such as by agitation or circulation. Preferably, the sample is kept in motion by continuously passing a small flow of electrolyte through the test cell. According to this preferred embodiment, a sample of electrolyte is continuously withdrawn from the purification or electrodeposition process, passed through the test cell and subsequently returned to the respective process. Electrolyte added to the cell may be adjusted to certain concentrations of the components of the electrolyte, such as, for example metal and acid content in order to reduce to a minimum any variation in the test method that may be caused by variations in component concentrations in the electrolyte.

For example, in the electrowinning of zinc, both the zinc and acid concentrations may be adjusted. Adjustment of the zinc level to 150 g/L could be used. Alternatively the zinc concentration could be adjusted to 55 g/L and the acid concentration to 150 g/L. Concentrations in the range of from 1 g/L to 250 g/L zinc and 0 to 250 g/l sulfuric acid are found to be equally satisfactory for use in the test cell. When using a continuous sample flow, excess electrolyte is discharged from the cell, for example, by means of an overflow.

The moving cathode is advanced through the cathode holder intermittently or continuously at a rate sufficient to allow inchoate deposition of metal. Preferably, the moving cathode is advanced continuously at a constant rate. The rate is dependent on the ratio between cathode length and cathode surface area, the value of the current density for inchoate deposition, the surface area of the cathode exposed to electrolyte, the fraction of exposed cathode area covered with deposited metal and the weight of deposited metal. The rate is also somewhat dependent on the degree of motion of electrolyte in the cell. Thus, the rate at which the cathode is moved through the cathode holder and, consequently, through the electrolyte, may vary in a range of values. At rates lower than the minimum rate, the measured overpotential will be that of metal onto that metal and will not be the activation overpotential of metal onto the moving cathode. At rates several orders of magnitude higher than the minimum rate, such as for example, one thousand times higher, the amount of metal deposited may be insufficient to obtain reliable and reproducible values for the activation overpotential. Preferably, the rate at which the cathode is moved is about ten to five hundred times the minimum rate. The minimum rate may be calculated by using the following formula:

$$R_{min} = \frac{abcd}{xy}, \text{cm/h,}$$

wherein:
a represents the cathode length to surface area ratio, $cm/cm^2$;
b represents current density, $A/cm^2$;
c represents cathode exposed area, $cm^2$;
d represents the electrochemical equivalent for the metal being deposited, g/Ah;
x represents the fraction of the exposed cathode area covered with metal; and
y represents the weight of deposited metal per unit of cathode surface area, $g/cm^2$.

When moving the cathode intermittently, the average rate of movement should be at least equal to the minimum rate for continuous movement, while the periods of time when the cathode is stationary should not exceed the period of time that will cause more than inchoate deposition.

A low current is applied to the anode and the moving cathode to cause inchoate deposition of metal onto the cathode. Preferably, the low current is controlled at a constant value. The current should be limited to low values, which only cause inchoate deposition. This is necessary to avoid the deposition of metal onto previously deposited metal whereby values of the overpotential are obtained of metal deposition onto that metal rather than values of the desired activation overpotential of metal deposition onto the moving cathode material. Thus, the deposition of too much metal should be avoided. Preferably, not more than about 10 to 30% of the cathode surface in contact with electrolyte should become covered with deposited metal at any time. Currents, expressed as current density, that cause inchoate deposition on the cathode moving at rates defined above should be at least 0.01 $mA/cm^2$. Current densities in respect of the moving cathode as hereafter discussed are to be taken as referring to the exposed area of the moving cathode. Below a value of the current, expressed as current density, of 0.01 $mA/cm^2$, special precautions may be required to obtain reliable measurements. For practical purposes, the current, expressed as current density, should be in the range of 0.01 to 4.0 $mA/cm^2$. Values of the current higher than the equivalent current density of 4.0 $mA/cm^2$ will require impractically high cathode movement rates. Preferably, current values, expressed as current density, are in the range of 0.1 to 0.4 $mA/cm^2$. For example, for inchoate copper deposition at a current density of 0.4 $mA/cm^2$ on a moving aluminum cathode, which has a ratio of length to surface area of 2.4, an exposed area of 0.25 $cm^2$ of which 20% is covered with deposited copper and on which $7 \times 10^{-3}$ g copper/$cm^2$ is deposited the minimum rate as calculated from the above formula is about 0.20 cm/h. Using the same values for the parameters, the minimum rate for lead is about 0.65 cm/h, for zinc is about 0.21 cm/h and that for manganese is about 0.17 cm/h.

The temperature of the electrolyte being measured may be maintained constant. Changes in temperature affect the measured activation overpotential, e.g., a decreasing temperature increases the measured overpotential. If desired, the cell and its contents are adjusted to and maintained at a suitable, controlled, constant temperature, which may be between 0° and 100° C., preferably between 20° and 75° C. If desired, the constant temperature may be approximately the same as the temperature of the electrolyte in the electrodeposition process and/or purification process, whichever is applicable. If the temperature is not maintained constant, the value of the activation overpotential should be corrected for the temperature variations so that the results of the tests are comparable.

The activation overpotential is measured continuously or intermittently and is recorded at the point of inchoate deposition of metal onto the moving cathode. For practical application of the method of this invention, the activation overpotential is expressed as the value of the measured overpotential at a current corresponding to a current density in the range of about 0.01 to 4.0 $mA/cm^2$ of exposed cathode area, preferably in the range of about 0.1 to 0.4 $mA/cm^2$. The activation overpotential is recorded on a suitable read-out instrument, or alternatively, recorded as a function of time. The recorded values of the overpotential are maintained in a preferred range. This is accomplished by making adjustments to the purification and electrodeposition processes when values of the overpotential deviate from the preferred range of values.

The activation overpotential has specific values for each metal dependent on the composition of the electrolyte. As every electrolyte composition can be purified to an optimum degree, has an optimum range of polarization affecting agent(s) contents and has an optimum range of polarization affecting agent(s) contents relative to its impurity content, the activation overpotential will similarly have a range of values that is required to yield the desired optimum results. Any one of a number of suitable polarization affecting agents known in the art may be used in the electrodeposition process of each metal. One of the most commonly used polarizing affecting agents is animal glue. I have determined that increasing concentrations of impurities may cause a decrease in activation overpotential, while increasing polarizing agent concentrations increase the overpotential, and increasing de-polarization agent concentrations decrease the overpotential.

If the value of the measured activation overpotential in the purification of electrolyte is too low, the impurity concentration is too high for optimum metal recovery in the electrodeposition process. Thus, dependent on the composition of the electrolyte, the activation overpotential is an indicator of the effectiveness of the purification process and deviations from optimum operation can be corrected by adjusting the purification process in relation to values of the activation overpotential, whereby the impurity concentration is lowered. Insufficiently purified electrolyte may be further purified in an additional purification step or by recirculation in the purification process. For example, in the electrowinning of zinc, correction of the zinc dust purification process may be accomplished by adjusting the temperature of the purification process, the duration of the purification process, increasing the amount of zinc dust used, or increasing the amount of a de-polarizing agent such as antimony, copper or arsenic present in ionic form in the electrolyte.

If the value of the activation overpotential measured for the electrolyte in the electrodeposition process is too low, the concentration of polarization affecting agent(s) in the electrolyte is insufficient to control cathodic metal deposition adequately, or the impurity concentration is too high relative to the concentration of polarization affecting agent(s). On the other hand, if the value is too high, the concentration of polarization affecting agent(s) is too high, and a resultant loss in efficiency and a rougher metal deposit occur. Thus, depending on the composition of the electrolyte, the activation overpotential is an indicator of the efficiency of the electrodeposition process and deviations from optimum operation can be corrected by changing the concentration or character of the polarization affecting agent(s) or by changing the concentration ratio between polarization affecting agent(s) and impurities in the electrolyte, as required in relation to values of the activation overpotential. Change in the concentration of polarization affecting agent(s) may be accomplished in a suitable manner such as by increasing or decreasing the rate of addition of polarization affecting agent(s) to the electrolyte. A decrease in the impurity concentration may be achieved by more effective purification of the electrolyte prior to the electrodeposition process. In the case of the presence of an excess concentration of polarization affecting agent(s) corrective action may also be taken by adding an agent to the electrolyte of opposite polarization affecting characteristics in a controlled fashion to bring the ratio of concentrations of impurities and polarization affecting agent(s) to the correct value. Adding a de-polarizing agent when required may be done conveniently by controlled addition of a metal salt, which acts as a depolarizing agent, which addition results in correcting the impurity to polarizing agent concentration ratio. For example, in the electrowinning of zinc, antimony in ionic form may be added as a depolarizing agent.

The method of the invention has a number of applications in processes for the electrodeposition of metals. Thus, the method can be used before, during and after purification of electrolyte and before, during and after the electrodeposition of metal from electrolyte.

For example, in the purification of zinc, sulfate electrolyte in the electrowinning of zinc, the method can be used to determine the degree of iron oxide removal, and the degree of removal by iron oxides of impurities such as arsenic, antimony and germanium.

In the electrodeposition process, the method can be advantageously used to determine the required amount of polarization affecting agent(s) alone and in relation to impurity concentration, the required amount of impurities in relation to concentration of polarization affecting agent(s), the need for adjustments to the electrolyte feed, or to electrolyte in process and the quality of recycled electrolyte.

The invention will now be described by means of the following non-limitative examples.

In the following examples, values of the activation overpotential were measured using a test cell having a sample volume of 500 ml. A volume of electrolyte was passed through the cell. Immersed in the electrolyte in the cell were a moving cathode consisting of a wire contained in and advanced through a stationary cathode holder fixedly positioned in the cell allowing 0.25 cm$^2$ of the cathode to be exposed to electrolyte, an anode and a SCE positioned between cathode and anode. The surface of the exposed area of the moving cathode was 4 cm away from the surface of the anode and the tip of the SCE was 1 cm away from the cathode such that the tip was not in direct line between the anode and the exposed area of the cathode. The temperature of the electrolyte flowing through the test cell was controlled at the desired value. The anode and the moving cathode were connected to a source of constant current and the SCE and the cathode were connected to the measuring means for the activation overpotential using a voltmeter with digital read-out and a recorder. A constant current was applied to cause inchoate deposition of metal on the moving cathode and values of the activation overpotential were measured and recorded. The fraction of the exposed cathode surface area covered with metal was 0.1.

EXAMPLE 1

This example illustrates how the activation overpotential measurements can be used to control the electrodeposition of copper. Values of the activation overpotential were measured using a current corresponding to a current density of 1.0 mA/cm$^2$. The cathode was a 1.19 mm diameter wire of No. 1100 aluminum alloy with a length to surface area ratio of 2.51 cm/cm$^2$. The minimum rate of movement of the cathode through the electrolyte was calculated to be 1.09 cm/h. The cathode was advanced through the cathode holder at 160 cm/h. The anode was a lead—0.75% silver anode. The electrolyte temperature was 50° C. and the electrolyte flow rate was 660 ml/min. Values of the measured activation overpotential were recorded on a recorder. The copper sulfate electrolyte contained 20 g/L copper and 150 g/L sulfuric acid, as well as varying added amounts of glue, chloride and antimony.

The electrodeposition process was carried out at a current density of 400 A/m$^2$ for a period of 24 hours. After the 24 hour deposition time, the deposit was analyzed for its surface quality and its ductility. The ductility was assessed by the number of times the deposit could be bent 180° before it showed cracking. The amounts of additives to the electrolyte, the average of the recorded values of the activation overpotential for each electrolyte composition and the qualitites of the electro deposited copper are given in Table 1.

TABLE 1

| Test No. | Additions to Electrolyte | | | Activation Overpotential mV | Ductility 180° bends No. | Nature of Deposit |
| --- | --- | --- | --- | --- | --- | --- |
| | glue mg/L | Cl$^-$ mg/L | Sb ions mg/L | | | |
| 1 | 0 | — | — | 118 | 10 | rough |
| 2 | 2.5 | — | — | 122 | 15 | rough |
| 3 | 5.0 | — | — | 132 | 14 | smooth |
| 4 | 7.5 | — | — | 140 | 20 | smooth |
| 5 | 10 | — | — | 142 | 15 | rough |
| 6 | 20 | — | — | 150 | 16 | rough |
| 7 | 0 | 1 | — | 129 | 29 | rough |
| 8 | 0 | 10 | — | 140 | 25 | rough |
| 9 | 0 | 30 | — | 145 | 10 | rough |
| 10 | 5 | 1 | — | 140 | 6 | smooth |
| 11 | 7.5 | 1 | — | 143 | 7 | rough |
| 12 | 5 | 10 | — | 180 | 7 | rough |
| 13 | 5 | 30 | — | 182 | 10 | rough |
| 14 | 0 | — | 300 | 118 | 12 | rough |
| 15 | 2.5 | — | 300 | 125 | 7 | smooth |
| 16 | 5 | — | 300 | 128 | 22 | smooth |
| 17 | 10 | — | 300 | 153 | 18 | rough |
| 18 | 20 | — | 300 | 164 | 7 | rough |
| 19 | 0 | 10 | 300 | 140 | 25 | rough |
| 20 | 5 | 10 | 300 | 178 | 23 | smooth |
| 21 | 30 | 10 | 300 | 203 | 11 | rough |
| 22 | 5 | 1 | 300 | 136 | 11 | smooth |
| 23 | 5 | 30 | 300 | 181 | 13 | smooth |
| 24 | 5 | 30 | 20 | 180 | 16 | smooth |

The results of tests 1-6 show that values for the activation overpotential increase with increasing amounts of glue in the electrolyte. In order to obtain a smooth deposit the activation overpotential should be controlled in the range of about 130 to 140 mV and the amount of glue in the electrolyte should be adjusted when the measured value of the activation overpotential is outside this range.

The results of tests 7-13 show that the presence of chloride in the electrolyte results in rough deposits, which in the additional presence of glue become also less ductile.

The results of tests 14-18 show that, when an electrolyte contains antimony and increasing amounts of glue, the values of the overpotential increase but that the results of the ductility test of the deposit become erratic. In order to correct this erratic behaviour, chloride should be present also. As can be seen from the results of tests 19-24, the presence of about 10 mg/L chloride as well as 5 mg/L glue give smooth and ductile deposits in the presence of antimony. In such a system, the values of the activation overpotential are about 180 mV and the system can be controlled at about this value by making judicious adjustments to the concentrations of either glue, or chloride or both.

EXAMPLE 2

This example illustrates how the activation overpotential measurements can be used to control the electrodeposition of manganese. Values of the activation overpotential were measured using a current corresponding to a current density of 1.0 mA/cm$^2$. The cathode was a 1.19 mm diameter wire of No. 1100 aluminum alloy with a length to surface area ratio of 2.51 cm/cm$^2$. The minimum rate of movement of the cathode through the electrolyte was calculated to be 0.92 cm/h. The cathode was advanced at a rate of 160 cm/h. The anode was a lead—0.75% silver anode. The electrolyte temperature was 50° C. and the electrolyte flow rate was 660 mL/min. Values of the measured activation overpotential were recorded on a recorder. The manganese sulfate electrolyte contained 45 g/L manganese sulfate, 135 g/L ammonium sulfate and 0.1 g/L sulfur dioxide, as well as varying added amounts of glue, copper, nickel, zinc and antimony. The pH of the electrolyte was 7.0. Electrodeposition of manganese at a current density of 400 A/m$^2$ requires the presence of 8 to 16 mg glue per liter of purified electrolyte to attain optimum current efficiency and smooth deposits. The values of the activation overpotential for electrolyte with specific additions are given in Table II.

TABLE II

| Additions to electrolyte in mg/L | | | | | Activation Overpotential in mV |
| --- | --- | --- | --- | --- | --- |
| glue | Cu | Ni | Zn | Sb | |
| 0 | — | — | — | — | 166 |
| 4 | — | — | — | — | 172 |
| 8 | — | — | — | — | 174 |
| 12 | — | — | — | — | 179 |
| 16 | — | — | — | — | 183 |
| 20 | — | — | — | — | 190 |
| 24 | — | — | — | — | 196 |
| 0 | 5 | — | — | — | 155 |
| 0 | 10 | — | — | — | 151 |
| 16 | 10 | — | — | — | 151 |
| 0 | — | 1 | — | — | 168 |
| 0 | — | 2 | — | — | 166 |
| 16 | — | 2 | — | — | 183 |
| 16 | 10 | 2 | — | — | 158 |
| 0 | — | — | 0.5 | — | 168 |
| 0 | — | — | 1 | — | 164 |
| 16 | — | — | 1 | — | 178 |
| 0 | — | — | — | 1 | 166 |
| 0 | — | — | — | 10 | 160 |
| 0 | — | — | — | 25 | 137 |
| 8 | — | — | — | 25 | 139 |
| 20 | — | — | — | 25 | 139 |
| 50 | — | — | — | 25 | 143 |
| 16 | — | — | 1 | 1 | 172 |
| 16 | — | — | 1 | 10 | 164 |

It can be seen from the tabulated results that glue acts as a polarizing agent, that copper, zinc and antimony act as de-polarizing agents and that nickel is essentially inactive. Thus, increasing amounts of glue have the effect of increasing the values of the activation overpotential while copper, zinc and antimony have the opposite effect. The results indicate also that the optimum glue levels in purified electrolyte of 8 to 16 mg/L result in values of the activation overpotential in the range of from 174 to 183 mV and that the amount of glue must be increased when de-polarizing agents (impurities) are present in small concentrations to return the values of the activation overpotential to within the desired range of 174 to 183. When concentrations of impurities higher than a few mg/L are present, the process for the purification of electrolyte should be enhanced. In this context it also follows from the test results that the effectiveness of the purification process can also be advantageously monitored by measuring the activation overpotential of the electrolyte.

EXAMPLE 3

This example illustrates how the activation overpotential measurements can be used to control the electrodeposition of nickel. Values of the activation overpotential were measured at 55° C. using a current corresponding to a current density of 1 mA/cm$^2$. The cathode was a 1.19 mm wire of copper with a length to surface area ratio of 2.51 cm/cm$^2$. The minimum rate of movement of the cathode through the electrolyte was calculated to be 0.98 cm/h. The cathode was advanced through the cathode holder at a rate of 160 cm/h. The anode was a lead—0.75% silver anode.

The electrolyte temperature was 55° C. and the electrolyte flow rate was 660 ml/min. Values of the measured activation overpotential were recorded on a recorder. The electrolyte contained 50 g/L nickel as nickel sulfate, 40 g/L sulfuric acid, 90 g/L sodium chloride and 16 g/L boric acid, as well as varying amounts of glue or sodium lauryl sulfate. Sodium lauryl sulfate is an addition agent in the electrowinning of nickel to prevent pitting of the deposited nickel and glue is added in electroplating of nickel as a levelling agent. The results are given in Table III.

TABLE III

| Additions to Electrolyte in mg/L | | |
|---|---|---|
| Sodium lauryl sulfate | Glue | Activation Overpotential in mV |
| 0 | — | 70 |
| 5 | — | 50 |
| 20 | — | 44 |
| — | 0 | 70 |
| — | 5 | 84 |
| — | 50 | 93 |

It can be seen from the results that sodium lauryl sulfate acts as a depolarizing agent and, when present in increasing amounts, lowers the values of the activation overpotential, and that glue acts as a polarizing agent and, when present in increasing amounts, increases the values of the activation overpotential. Values of activation overpotential can be maintained at desired values by adjusting the concentration of the addition agent that change polarization.

EXAMPLE 4

This example illustrates how the activation overpotential measurements can be used to control the electrodeposition of lead. Values of the activation overpotential were measured using a current corresponding to a current density of 4.0 mA/cm$^2$. The cathode was a 1.19 mm diameter wire of copper with a length to surface area ratio of 2.51 cm/cm$^2$. The minimum rate of movement of the cathode through the electrolyte was calculated to be 13.8 cm/h. The cathode was advanced through the cathode holder at a rate of 160 cm/h. The anode was a lead—0.75% silver anode.

The temperature of the electrolyte was 40° C. and the electrolyte flow rate was 660 mL/min. Values of the measured activation overpotential were recorded on a recorder. The lead fluosilicate electrolyte contained 75 g/L lead as lead fluosilicate, 90 g/L fluosilicic acid, as well as varying amounts of ECA (Aloes extract), lignin sulfonate and sodium thiosulfate. Electrolysis was carried out for 24 hours at 200 A/m$^2$ and at 40° C. using lead bullion electrodes to obtain a lead deposit. The quality of the lead deposite was determined.

The additions to the electrolyte, the activation overpotential and the nature of the lead deposit for each test are given in Table IV.

TABLE IV

| Addition to Electrolyte | | | | |
|---|---|---|---|---|
| ECA mg/L | lignin Sulfonate mg/L | Sodium thiosulfate mg/L | Activation Overpotential mV | Nature of Deposit |
| 0 | 0 | 0 | 16 | rough |
| 0 | 4 | 0 | 35 | rough |
| 0.5 | 4 | 0 | 40 | rough |
| 1.0 | 4 | 0 | 43 | rough |
| 1.5 | 4 | 0 | 46 | smooth |
| 2.0 | 4 | 0 | 52 | smooth |
| 3.0 | 4 | 0 | 58 | rough |
| 3.0 | 4 | 50 | 18 | rough |

From the results in Table IV can be seen that both ECA and lignin sulfonate act as polarizing agents and sodium thiosulfate acts as a de-polarizing agent. In electrodeposition of lead the amount of lignin sulfonate is usually maintained substantially constant, while the amount of ECA is adjusted to maintain the activation overpotential in the desired range of 45 to 55 mV in order to obtain a smooth and level lead deposit. When the desired values of the activation overpotential are exceeded, sodium thiosulfate can be added to return the value of the activation overpotential to within the desired range.

The following examples relate to the electrowinning of [glue] zinc. The moving cathode was a 1.19 mm diameter wire of No. 4043 aluminum alloy, with a length to surface area ratio of 2.51 cm$^2$/cm. The anode was a lead-silver alloy containing 0.75% silver. The minimum rate for cathode movement was calculated to be 1.06 cm/h.

EXAMPLE 5

This example illustrates the effects of variations in the values of the applied current expressed as current density, the cathode wire speed, the temperature of the electrolyte and the flowrate of the electrolyte. A quantity of plant electrolyte was analyzed and adjusted to 55 g/L Zn and 150 g/L H$_2$SO$_4$. The adjusted electrolyte also contained 0.01 mg/L Sb, 0.03 mg/L Cu, 0.1 mg/L Co. 0.1 mg/L Ni, 0.005 mg/L Ge, 0.5 mg/L Cd, 30 mg/L Cl and 2 mg/L F. Adjsted electrolyte was continuously passed through the test cell and the activation overpotential measured and recorded as described. The results are tabulated in Table VA.

TABLE V A

| Test No. | Current density mA/cm$^2$ | Moving cathode speed cm/hr | Temperature of electrolyte °C. | Flow rate of electrolyte mL/min | Activation overpotential mV |
|---|---|---|---|---|---|
| 55 | 0.1 | 60 | 30 | 668 | 10 |
| 56 | 1.0 | 60 | 30 | 668 | 75 |
| 57 | 1.0 | 180 | 30 | 668 | 82 |
| 58 | 1.0 | 300 | 30 | 668 | 90 |
| 59 | 1.0 | 60 | 21 | 668 | 83 |
| 60 | 1.0 | 60 | 35 | 668 | 55 |
| 61 | 1.0 | 60 | 60 | 668 | 20 |
| 62 | 1.0 | 60 | 30 | 100 | 70 |
| 63 | 0.4 | 60 | 30 | 668 | 35 |
| 64 | 2.0 | 60 | 30 | 668 | 75 |
| 65 | 4.0 | 60 | 30 | 668 | 115 |

The results clearly indicate the effect of variables in the method and the need for using standardized conditions for practical application.

EXAMPLE 6

This examples illustrates the effects of varying amounts of antimony, germanium, cobalt and glue added to adjusted electrolyte with the composition as in Example 5. The activation overpotential was measured using a current corresponding to a current density of 1.0 ma/cm², a cathode speed of 160 cm/hr, an electrolyte temperature of 35° C., and an electrolyte flow rate of 660 mL/min. Values of the measured activation overpotential were recorded on an x-y recorder. The results are tabulated in Table VI. In the Table, the values of the overpotential represent the average recorded value.

TABLE VI

| Test No. | Additions, in mg/L |  |  |  | Activation overpotential m/V |
|---|---|---|---|---|---|
|  | Glue | Sb | Ge | Co |  |
| 66 | 0 | 0 | 0 | 0 | 80 |
| 67 | 10 | 0 | 0 | 0 | 98 |
| 68 | 20 | 0 | 0 | 0 | 110 |
| 69 | 30 | 0 | 0 | 0 | 120 |
| 70 | 0 | 0.02 | 0 | 0 | 58 |
| 71 | 10 | 0.02 | 0 | 0 | 89 |
| 72 | 20 | 0.02 | 0 | 0 | 106 |
| 73 | 30 | 0.02 | 0 | 0 | 109 |
| 74 | 0 | 0.04 | 0 | 0 | 53 |
| 75 | 10 | 0.04 | 0 | 0 | 90 |
| 76 | 30 | 0.04 | 0 | 0 | 96 |
| 77 | 5 | 0.06 | 0 | 0 | 76 |
| 78 | 0 | 0.08 | 0 | 0 | 50 |
| 79 | 10 | 0.08 | 0 | 0 | 78 |
| 80 | 30 | 0.08 | 0 | 0 | 83 |
| 81 | 0 | 0 | 0.04 | 0 | 70 |
| 82 | 30 | 0 | 0.04 | 0 | 116 |
| 83 | 0 | 0.04 | 0 | 2.0 | 55 |
| 84 | 30 | 0.04 | 0 | 2.0 | 105 |

The results indicate that increasing concentrations of glue increase the activation overpotential and that increasing concentrations of impurities decrease the activation overpotential of zinc.

EXAMPLE 7

This example illustrates that increasing concentrations of glue are required to give good current efficiency when increasing impurity concentrations are present in electrolyte and that optimum ranges for glue concentrations in relation to impurity concentrations exist to give highest current efficiencies. Samples of adjusted plant electrolyte as used in Example 6, to which varying amounts of glue and antimony and/or cobalt were added as potassium antimony tartrate and cobalt sulfate, respectively, were subjected to electrolysis in a cell at a current density of 400 A/m² at 35° C. for 24 hours. The current efficiencies for the zinc deposition were determined by determining the ratio of the weight of the deposited zinc to the calculated weight based on the total amount of current passed through the cell for the deposition of zinc. The results are given in Table VI.

TABLE VII

| Test No. | Sb added in mg/L | Co added in mg/L | Glue added in mg/L |  |  |  |  |  |  |  |
|---|---|---|---|---|---|---|---|---|---|---|
|  |  |  | 0 | 10 | 15 | 20 | 25 | 30 | 40 | 45 | 50 |
|  |  |  | Current efficiencies in % |  |  |  |  |  |  |  |
| 85 | 0.01 | 0 | 88 | 92 | 91 | 90 | 89 | 88 | 87 | 87 | 85 |
| 86 | 0.03 | 0 | 79 | 90 | 92 | 93 | 92 | 91 | 89 | 88 | 87 |
| 87 | 0.05 | 0 | 56 | 86 | 90 | 92 | 93 | 93 | 92 | 91 | 88 |
| 88 | 0.07 | 0 | 43 | 72 | 81 | 85 | 89 | 92 | 93 | 92 | 89 |
| 89 | 0.01 | 0.05 | 89 | 92 | 92 | 91 | 90 | 89 | 88 | 87 | 85 |
| 90 | 0.01 | 2 | 88 | 92 | 92 | 92 | 92 | 91 | 91 | 90 | 89 |
| 91 | 0.01 | 5 | 65 | 87 | 92 | 92 | 92 | 92 | 92 | 92 | 91 |
| 92 | 0.01 | 5* | — | 43 | 74 | 82 | 82 | 81 | 79 | 77 | 75 |
| 93 | 0.03 | 0.05 | 80 | 90 | 92 | 93 | 93 | 91 | 90 | 88 | 86 |
| 94 | 0.03 | 1 | 40 | 74 | 85 | 92 | 94 | 93 | 92 | 91 | 89 |
| 95 | 0.03 | 5 | — | 58 | 74 | 87 | 92 | 94 | 94 | 93 | 90 |
| 96 | 0.03 | 5* | — | — | — | 40 | 72 | 82 | 83 | 83 | 78 |

*48 hour deposit

It is evident from the tabulated results that for each antimony concentration, a corresponding narrow range of glue concentrations was required to give the highest possible current efficiencies. Current efficiencies decreased for both deficient and excessive glue concentrations. Thus, a range of optimum glue concentrations exists for each antimony concentration. Similarly, when antimony and cobalt are present, glue additions are required to counteract the harmful effects of these impurities and optimum glue concentrations exist for each antimony and cobalt concentration. The optimum glue concentrations were the same for 48 hours as for 24 hours deposits, but the current efficiencies had decreased.

EXAMPLE 8

Values for the activation overpotential for glue and impurities concentrations obtained in tests as illustrated in Examples 5 and 6 and Tables VA and VI were combined with ranges of maximum current efficiencies for combinations of concentrations of glue and impurities obtained in tests as illustrated in Example 7 and Table VII. Thus, the following ranges of values for optimum current efficiency were obtained in relation to ratios between glue and impurities as indicated by the values of the activation overpotential. The ranges are tabulated in Table VII.

TABLE VII

| Activation overpotential in mV | Range of current efficiency in % |
|---|---|
| 75 | 75–83 |
| 80 | 79–86 |
| 85 | 83–89 |
| 90 | 86–91 |
| 95 | 88–93 |
| 100 | 90–94 |
| 105 | 90–94 |
| 110 | 89–93 |
| 115 | 87–92 |
| 120 | 86–89 |
| 125 | 83–87 |

It can be seen from the tabulated figures that the highest ranges of current efficiencies are obtained when the activation overpotential is maintained in the range of 90 to 115 mV, measured at 35° C.

EXAMPLE 9

This example illustrates that the activation overpotential measurements can be used to determine whether the correct glue concentration is present in the electrolyte relative to the impurity concentration and what changes are required in glue concentration to optimize the zinc electrowinning process. Using the same electrolyte as used in previous examples, tests as described in Example 6 were repeated, current efficiencies were determined as in Example 7 and the results combined as illustrated in Example 8. Using the results of the tests according to this example, the required change in glue concentration in mg/L was determined at measured values for the activation overpotential to obtain the optimum value for the current efficiency in the electrolytic process. Data presented in Table IX show the program to control the electrowinning process for zinc by making specified changes in glue concentration in zinc electrolyte.

TABLE IX

| Measured activation overpotential in mV at 35° C. | Required change in glue concentration in mg/L for optimum current efficiency |
|---|---|
| 75 | increase by 9 |
| 80 | increase by 7 |
| 85 | increase by 5 |
| 90 | increase by 3 |
| 95 | increase by 1 |
| 100 | no change |
| 105 | no change |
| 110 | decrease by 1 |
| 115 | decrease by 3 |
| 120 | decrease by 5 |
| 125 | decrease by 7 |
| 130 | decrease by 9 |

EXAMPLE 10

This example illustrates that antimony can be used in relation to measured values of the activation overpotential to control the zinc electrowinning process at optimum current efficiency.

In a series of electrowinning cells using an acidic zinc sulfate electrolyte, having the adjusted composition as given in Example 5, both glue and antimony are added. Glue is added to the electrolyte at a constant rate of 20 mg/L, while antimony is normally added at a rate of 0.04 mg/L.

Using the electrolyte and the above mentioned additions of glue and antimony, activation over potentials and current efficiencies were determined as in Example 9. Optimum values for current efficiencies were attained with activation overpotentials of 100 to 105 mV. Using the results of these determinations, the required changes in antimony concentrations in the electrolyte in mg/L were determined at measured values for the activation overpotential to obtain the optimum value for the current efficiency in the electrolytic process. The control program is given in Table X.

TABLE X

| Measured activation overpotential in mV | Required change in antimony concentration in mg/L for optimum current efficiency |
|---|---|
| 85 | decrease by 0.03 |
| 90 | decrease by 0.02 |
| 95 | decrease by 0.01 |
| 100 | no change |
| 105 | no change |
| 110 | increase by 0.01 |
| 115 | increase by 0.02 |
| 120 | increase by 0.03 |

EXAMPLE 11

This example illustrates that the removal of impurities from neutral zinc electrolyte by cementation with zinc dust can be monitored by activation overpotential measurements. Impure plant electrolyte was subjected to purification with varying amounts of zinc dust added to the electrolyte containing previously added antimony as antimony potassium tartrate in varying amounts. Cementation was carried out at 50° C. with agitation and using a retention time of one hour. A flow of purified electrolyte was filtered and cooled to 35° C. The flow was then passed through the test cell for measurement of the activation overpotential. The purified electrolyte was analyzed to determine impurity concentrations. The results are tabulated in Table XI.

TABLE XI

| Sb added in mg/L | Zinc dust added in g/L | Activation overpotential in mV | Impurities in purified electrolyte in mg/L | | | | |
|---|---|---|---|---|---|---|---|
| | | | Cd | Cu | Co | Ni | Sb |
| 0.75 | 0 | 34 | 200 | 3.5 | 1.6 | 1.8 | 0.75 |
| 0.75 | 0.5 | 48 | 21 | 4.1 | 0.3 | 0.9 | 0.09 |
| 0.75 | 1.0 | 64 | 12 | 3.4 | 0.3 | 0.5 | 0.05 |
| 0.75 | 1.5 | 74 | 3.9 | 1.3 | 0.2 | 0.6 | 0.04 |
| 0.75 | 2.0 | 76 | 1.9 | 1.0 | 0.2 | 0.4 | 0.03 |
| 0.75 | 2.5 | 88 | 0.4 | 0.8 | 0.3 | 0.3 | 0.03 |
| 0.75 | 3.0 | 94 | 0.3 | 0.6 | 0.2 | 0.2 | 0.02 |
| 0.25 | 2.0 | 70 | 2.2 | 0.5 | 0.2 | <0.1 | 0.07 |
| 0.50 | 2.0 | 74 | 2.2 | 0.6 | 0.1 | 0.1 | 0.03 |
| 1.00 | 2.0 | 85 | 0.6 | 0.6 | 0.1 | <0.1 | 0.02 |

EXAMPLE 12

This example illustrates how the activation overpotential measurements such as those given in Example 11 can be used to determine what corrections must be made to the process for controlling variables such as zinc dust and antimony additions to optimize the zinc dust purification of electrolyte. Data presented in Table XII show the program to control the zinc dust purification process by making specified changes in zinc dust or antimony salt additions to the zinc electrolyte during purification if the measured activation overpotential indicate purification has not proceded to completion.

TABLE XII

| Measured activation overpotential in mV for neutral electrolyte | Required additions of | |
|---|---|---|
| | zinc dust (g/L) | Sb (mg/L) |
| 80 | 0 | 0 |
| 75 | 0 | 0 |
| 70 | 0.3 | 0.1 |
| 65 | 0.6 | 0.2 |
| 60 | 0.9 | 0.3 |
| 55 | 1.2 | 0.4 |
| 50 | 1.5 | 0.5 |
| 45 | 1.8 | 0.5 |
| 40 | 2.1 | 0.5 |

What I claim as my invention is:

1. A method for controlling a process for the electro deposition of a metal using an electrolyte containing concentrations of impurities, said method comprising the steps of establishing a test cell, a sample of electrolyte, a moving cathode, made of an electrically conductive material other than the metal being deposited, which moving cathode has an area exposed to said electrolyte, an anode, and a reference electrode, said electrodes being immersed in said sample, a constant current supply and measuring means electrically connected to said electrodes; applying a low current to the electrodes in said test cell, said current being sufficient to cause inchoate desposition of said metal or said cathode; measuring the activation overpotential at the point of inchoate deposition of said metal; relating the measured activation overpotential to the concentration of impurities in said sample; and adjusting the concentration of impurities in the electrolyte of the process for the deposition of metal to obtain optimum deposition of metal, wherein inchoate deposition is defined as the deposition of metal which has just begun and is limited to a partial covering of the moving cathode surface by deposited metal.

2. A method for controlling a process for the electro deposition of a metal using electrolyte containing concentrations of at least one polarization affecting agent, said method comprising the steps of establishing an electrolytic test circuit comprising a test cell, a sample of electrolyte, a moving cathode made of an electrically conductive material other than the metal being deposited, which moving cathode has an area exposed to said electrolyte, an anode and a reference electrode, said electrodes being immersed in said sample, a constant current supply and measuring means electrically connected to said electrodes; applying a low current to the electrodes in said test cell, said current being sufficient to cause inchoate deposition of said metal on said cathode; measuring the activation overpotential at the point of inchoate deposition of said metal; relating the measured activation overpotential to the concentration of said at least one polarization affecting agent in said sample; and adjusting the concentration of said polarization affecting agent in the electrolyte to obtain optimum efficiency and level metal deposits in the elctro-deposition process, wherein inchoate deposition is defined as the deposition of metal which has just begun and is limited to a partial covering of the moving cathode surface by deposited metal.

3. A method for controlling a process for the electro deposition of a metal using electrolyte containing concentrations of impurities and of at least one polarization affecting agent, said method comprising the steps of establishing an electrolytic test circuit comprising a test cell, a sample of electrolyte, a moving cathode made of an electrically conductive material other than the metal being deposited, which moving cathode has an area exposed to said electrolyte, an anode and a reference electrode, said electrodes being immersed in said sample, a constant current supply and measuring means electrically connected to said electrodes; applying a low current to the electrodes in said test cell current being sufficient to cause inchoate deposition of said metal on said cathode; measuring the activation overpotential at the point of inchoate deposition of said metal; relating the measured activation overpotential to the concentration ratio between impurities and said at least one polarization affecting agent in said sample; and adjusting the concentration ratio in the process electrolyte to obtain optimum efficiency and level metal deposits in the electro deposition process, wherein inchoate deposition is defined as the deposition at metal which has just begun and is limited to a partial covering of the moving cathode surface by deposited metal.

4. A method as defined in claim 2 or 3 wherein the concentration of polarization affecting agents is adjusted by either increasing the amount of agent already present, or by adding a second polarization affecting agent of opposite polarization affecting characteristics to the polarization affecting agent already present.

5. A method as defined in claim 3 wherein the concentration ratio is adjusted by changing the concentration of impurities in the electrolyte.

6. A method as defined in claim 3 wherein the concentration ratio is adjusted by changing the concentration of polarization affecting agents in the electrolyte.

7. A method as defined in claim 6 wherein the concentration of polarization affecting agents is changed by either increasing the amount of agent already present, or by adding a second polarization affecting agent of opposite polarization affecting characteristics to the polarization affecting agent already present.

8. A method as defined in claim 1, 2, or 3, wherein the value of said current corresponds to a value of corresponding current density in the range of 0.01 to 4.0 $mA/cm^2$, based on the exposed area of the moving cathode.

9. A method as defined in claim 1, 2, or 3, wherein said low current has a constant value.

10. A method as defined in claim 1, 2, or 3, wherein the activation overpotential is measured continuously.

11. A method as defined in claim 1, 2, or 3, wherein the activation overpotential is measured intermittently.

12. A method as defined in claim 1, 2, or 3, wherein said sample of electrolyte is kept in motion.

13. A method as defined in claim 1, 2, or 3, wherein said sample of electrolyte is kept in motion by continuously passing a flow of electrolyte through said test cell.

14. A method as defined in claim 1, 2, or 3, wherein the value of said current being sufficient to cause inchoate deposition of metal is sufficient to cause not more than 10 to 30% of the surface area of the moving cathode which is exposed to electrolyte to become covered with deposited metal.

15. A method as defined in claim 1, 2, or 3, wherein the moving cathode is advanced at a substantially constant rate.

16. A method as defined in claim 1, 2, or 3, wherein the moving cathode is continuously advanced.

17. A method as defined in claim 1, 2, or 3, wherein the moving cathode is advanced in intermittent fashion.

18. A method as defined in claim 1, 2, or 3, wherein the moving cathode is advanced through the sample of electrolyte at a substantially constant rate, said substantially constant rate being at least equal to a minimum rate defined by the following formula:

$$R_{min} = \frac{abcd}{xy}, \text{cm/h},$$

wherein:
a represents the cathode length to surface area ratios, $cm/cm^2$;
b represents current density, $A/cm^2$;
c represents cathode exposed area, $cm^2$;
d represents the electrochemical equivalent for the metal being deposited, g/Ah;
x represents fraction of cathode covered with metal;
y represents the weight of deposited metal per unit of cathode surface area, $g/cm^2$.

19. A method as defined in claim 1, 2, or 3, wherein the moving cathode is advanced through the sample of electrolyte at a substantially constant rate, said rate being in the range of 10 to 500 times the minimum rate, said minimum rate being defined by the following formula:

$$R_{min} = \frac{abcd}{xy}, \text{cm/h},$$

wherein:
a represents the cathode length to surface area ratios, $cm/cm^2$;
b represents current density, $A/cm^2$;

c represents cathode exposed area, cm$^2$;

d represents the electrochemical equivalent for the metal being deposited, g/Ah;

x represents fraction of cathode covered with metal;

y represents the weight of deposited metal per unit of cathode surface area, g/cm$^2$.

20. A method as defined in claim 1, 2, or 3, wherein the electrolyte in the test cell is kept at a substantially constant temperature and wherein the constant temperature selected is between 20° C. and 75° C.

21. A method as defined in claim 1, 2, or 3, wherein the electrolyte is a sulfate-based electrolyte and wherein the moving cathode in the test cell is a wire made of a material chosen from aluminum and suitable aluminum alloys.

22. A method as defined in claim 1, 2, or 3, wherein the electrolyte is a sulfate-based electrolyte and wherein the moving cathode in the test cell is a strip made of a material chosen from aluminum and suitable aluminum alloys.

23. A method as defined in claim 1, 2, or 3, wherein the electrodes are positioned in the cell in fixed relation to one another.

24. A method as defined in claim 1, 2, or 3, wherein the measuring of the activation overpotential is effected by recording values of said activation overpotential as a function of time.

25. A method as defined in claim 1, 2, or 3, wherein said metal is chosen from zinc, copper, lead, iron, cobalt, nickel, manganese, chromium, tin, cadmium, bismuth, indium, silver, gold, rhodium and platinum.

26. A method as claimed in claim 2 or 3, wherein the metal being electrodeposited is chosen from zinc, copper, manganese, or nickel, and the polarization affecting agent is animal glue.

27. A method as defined in claim 1, 2, or 3, wherein the metal being electrodeposited is chosen from lead and nickel, and the moving cathode is a wire made of copper.

28. A method as defined in claim 1, 2 or 3, wherein the metal is chosen from zinc, copper and manganese, and said moving cathode is a wire made of a material chosen from aluminum and aluminum alloys.

29. A method as defined in claim 5 wherein the metal being deposited is zinc, and wherein the concentration ratio is adjusted by changing the concentration of antimony in the electrolyte.

30. A method as defined in claim 6 wherein the metal being deposited is zinc and wherein the concentration ratio is adjusted by changing the effective concentration of polarization affecting agent in the electrolyte.

31. A method as defined in claim 30 wherein the polarization affecting agent is animal glue.

32. A method according to claim 31 wherein the concentration ratio is adjusted by adjusting the concentration of glue to a value at which the activation overpotential measured at a temperature of between 25° C. and 40° C. is in the range of 70 to 150 millivolts, and wherein the activation overpotential is measured at a value of a low constant current corresponding to a current density in the range of 0.01 to 4.0 A/cm$^2$, based on the exposed area of the moving cathode.

33. A method according to claim 32 wherein the value of the corresponding current density is in the range of 0.1 to 0.4 A/cm$^2$.

34. A method as defined in claim 3 wherein the concentration ratio in the electrolyte is adjusted by changing simultaneously the concentration of the impurities and the concentration of said at least one polarization affecting agent.

35. A method as defined in claim 32 or 33 wherein the concentration of glue is increased when the measured value of the activation overpotential decreases to below about 70 mV, and wherein the concentration of glue is decreased when the measured value of the activation overpotential increases to above 150 mV.

36. A method as defined in claim 5 wherein the metal being deposited is zinc, the polarization affecting agent is animal glue, and the impurity is dissolved antimony, and wherein the concentration ratio is adjusted by adjusting the concentration of antimony to a value at which the activation overpotential measured at a temperature of between 25° C. and 40° C. is in the range of 70 to 150 millivolts, and wherein the activation overpotential is measured at a value of a low constant current corresponding to a current density in the range of 0.01 to 4.0 A/cm$^2$, based on the exposed area of the moving cathode.

37. A method as defined in claim 36 wherein the value of the corresponding current density is in the range of 0.1 to 0.4 A/cm$^2$.

38. A method as defined in claims 32 or 33 wherein the concentration of antimony is increased when the measured value of the activation overpotential decreases to below about 70 mV, and wherein the concentration of antimony is decreased when the measured value of the activation overpotential increases to above 150 mV.

* * * * *